US00PP10627P

United States Patent [19]

DeClercq

[11] Patent Number: Plant 10,627

[45] Date of Patent: Sep. 29, 1998

[54] SPATHIPHYLLUM PLANT NAMED 'JUNGFRAU'

[75] Inventor: Danny DeClercq, Destelbergen, Belgium

[73] Assignee: Twyford International, Inc., Santa Paula, Calif.

[21] Appl. No.: 833,141

[22] Filed: Apr. 4, 1997

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

A Spathiphyllum plant named 'Jungfrau' characterized by its miniature growth habit, satin texture foliage, and oblong white spathes. Plants of 'Jungfrau' grow very quickly to marketable size, bloom and re-bloom quickly, and are adaptable to a variety of pot sizes from 6 cm through 20 cm. Plants of 'Jungfrau' are responsive to growth regulators used to induce uniform flowering and branching, and are more resistant to common soil-borne pathogens than plants of comparison cultivar 'Petite'. These combined characteristics make 'Jungfrau' a unique new cultivar.

4 Drawing Sheets

The present invention comprises a new and distinct cultivar of Spathiphyllum, botanically known as *Spathiphyllum hybrid*, and referred to by the cultivar name 'Jungfrau'.

The new cultivar is the product of a breeding program carried out by the inventor Danny De Clercq in Lochristi, Belgium. The new cultivar 'Jungfrau' is the result of a cross of the following parent plants made by the inventor in Lochristi, Belgium in December 1989:

> Seed parent: Spathiphyllum No. 5—A selection of Spath. Mauna Loa 'Supreme', selected and maintained by the inventor and used only for breeding purposes. × Pollen parent: Spathiphyllum No. 7A—A mutation of Spath. 'Petite', selected and maintained by the inventor and used only for breeding purposes.

The new cultivar 'Jungfrau' was discovered and selected in July 1992 by the inventor from a group of seedlings resulting from the stated cross. Propagation by tissue culture performed in Lochristi, Belgium under the supervision of the inventor was used to increase the number of plants for evaluation and has demonstrated the stability of the combination of characteristics from generation to generation.

The following observations, measurements and values describe plants grown in Apopka, Fla. under greenhouse condition which closely approximate those generally used in horticultural practice.

The following traits have been repeatedly observed to be characteristics which in combination distinguish 'Jungfrau' from other Spathiphyllum of the same general type, for example, the unpatented cultivar 'Petite' to which comparative reference is made.

1. Plants of 'Jungfrau' have a miniature growth habit, and are ideally suited for 6 cm, 9 cm, or 11 cm pots. However, the variety is versatile, and may be finished in pots as large as 20 cm.

2. The leaves of 'Jungfrau' are of intermediate width with a satin texture surface. In comparison, the leaves of 'Petite' are narrow with a shiny surface.

3. Plants of 'Jungfrau' bloom earlier, remain in bloom longer, and rebloom in less time than plants of 'Petite'.

4. The flower petioles of 'Jungfrau' are shorter than those of 'Petite'.

5. Plants of 'Jungfrau' are more resistant to diseases caused by soil borne pathogens than plants of 'Petite'.

All color references are measured against The Royal Horticultural Society color chart. Colors are approximate as color depends on horticultural practices such as light level and fertilization rate, among others, without, however, any variance in genotype.

In the accompanying color photographic drawings,

The photo on sheet 1 depicts a 26 week old plant of 'Jungfrau' in a 10 cm pot initiated from a single microcutting obtained by tissue culture and grown under appropriate growing conditions.

The photograph on sheet 2 depicts small plants of 'Jungfrau' blooming in 6 cm cell trays approximately 22 weeks after planting single microcuttings in each cell.

The photos on sheets 3 and 4 depict plants of 'Jungfrau' blooming in 15 cm and 20 cm pots, respectively, with the plants being approximately 36 and 44 weeks old, respectively, and grown from single microcuttings.

Colors are as accurate as possible with color illustrations of this type. The following description is based on the plant illustrated in Sheet 1.

Origin: Seedling selected from cross described above.

Classification: *Spathiphyllum hybrid*, cv, 'Jungfrau'.

Propagation: Asexual production either by tissue culture or division.

Inflorescence:

*Immature*.—The spathe is tightly rolled around the spadix and emerges from the petiole sheath. The spathe is fully open when the peduncle is fully elongated, approximately 20 cm to 28 cm above the soil surface.

*Mature*.—Spathe: Size: The spathe is approximately 6.5 cm 8 cm in length and 2.6 cm to 3.3 cm in width. It is cupped, with the depth of the cups being about 1.0 cm. Color: Fully open: Upper surface: Pure white 155 D. Lower surface: Pure white 155 D. Midrib and apex: 145 A. Small flowers arising from small axillary branches are typically streaked with 145 A along primary veins. Faded: Upper surface: 155 D flushed with 145 C. Lower surface: 155 D flushed with 145 B-C. Midrib and apex: 144 A. Arrangement: The spathe terminates from a straight peduncle which opens vertically above the leaves. Shape: The spathe is ovate with an attenuate to cuneate base and an elongated acute to cuspidate apex. Flowering: Depending on season, approximately 3 to 7 blossoms will be present on plants, as illustrated in the photo on Sheet 1. Smaller, narrower blossoms may occur on less mature growth.

Floral organs:

*Spadix*.—Size: Approximately 1.9 cm to 2.6 cm in height and 0.8 cm to 1.0 cm in width. Color: When the spathe unrolls, the spadix is 158 B-C gradually changing to 145 A. Stamens: Anthers and filaments are minute and not clearly visible. Pollen: 155 D. Pistil: White in color, conical, protruding between the staminate flowers, firmly fixed to the main axil. The pistillate flowers extend approximately 2 mm beyond the staminate flowers.

General appearance:

*Plant*.—Under appropriate growing conditions, 'Jungfrau' attains a size of approximately 14.5 cm to 16.0 cm in height and 20 cm to 26 cm in width.

*Leaves*.—Form: The leaf blade is ovate with an acute apex and a cuneate base. The margins are entire and slightly wavy. The midrib tends to curve over the length of the leaf. The leaf blade is typically curved downward at the tip. The leaf surface is satin textured. Size: Leaf blades are approximately 10.5 cm to 15.3 cm in length and 4.5 cm to 5.9 cm in width. Petiole: The petiole is approximately 7.5 cm to 11.6 cm in height from the base of the petiole to the base of the leaf blade on the primary shoot. Secondary shoots are smaller depending on the age of the shoot. The petiole is about 3 mm in diameter at the junction of the geniculum and petiole sheath. The petiole below the geniculum is straight. Petiole sheath: The petiole sheath is approximately 6.4 cm to 9.9 cm in length and 3 mm to 5 mm in width at midpoint. The tip of the petiole sheath is rounded. There is no space between the top of the petiole sheath and the base of the geniculum. Geniculum: The geniculum is approximately 1.1 to 1.7 cm in length and 3 mm in diameter, and is straight. The color is 147 B. Veins: Veins are sunken, with the leaf blade convex between veins on the upper surface. The midrib is sunken. Well defined primary veins radiate out from the midrib over the length of the leaf. There are approximately 9 pairs of primary veins on the leaf. Color: Upper surface: 137 A. Lower surface: 147 B. Midrib, upper surface: 137 A-B. Midrib, lower surface: 145 B. Petiole: 147 A-B. Petiole sheath: 147 A-B. Roots: White fleshy roots with fine laterals.

I claim:

1. A new and distinct cultivar of Spathiphyllum plant named 'Jungfrau', as illustrated and described.

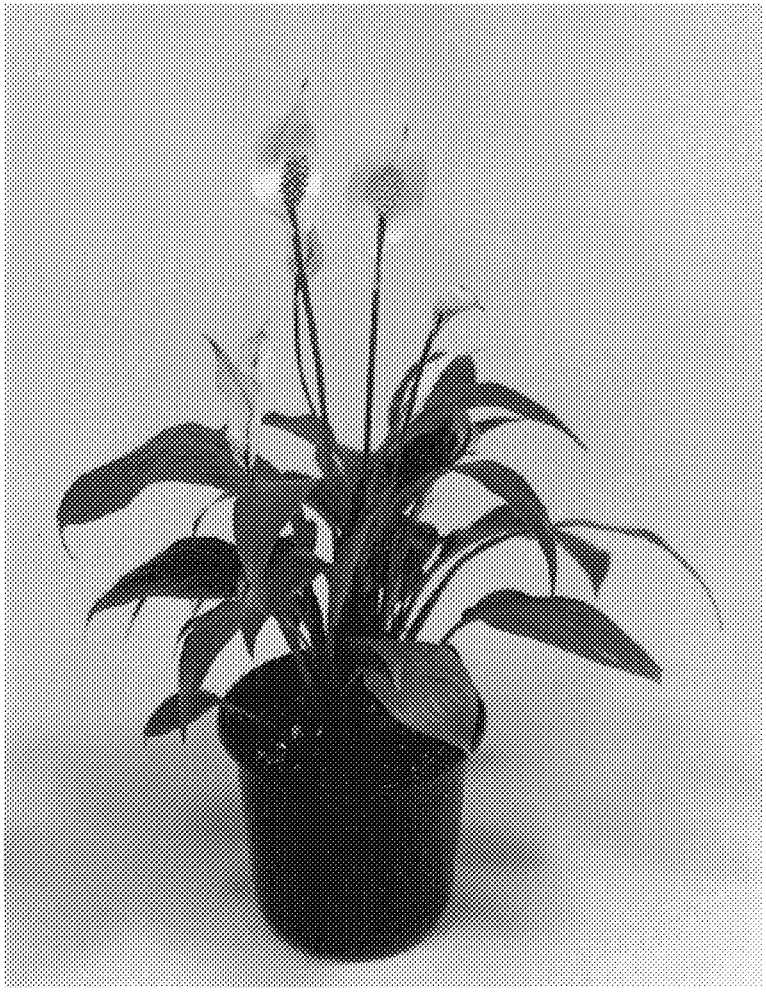

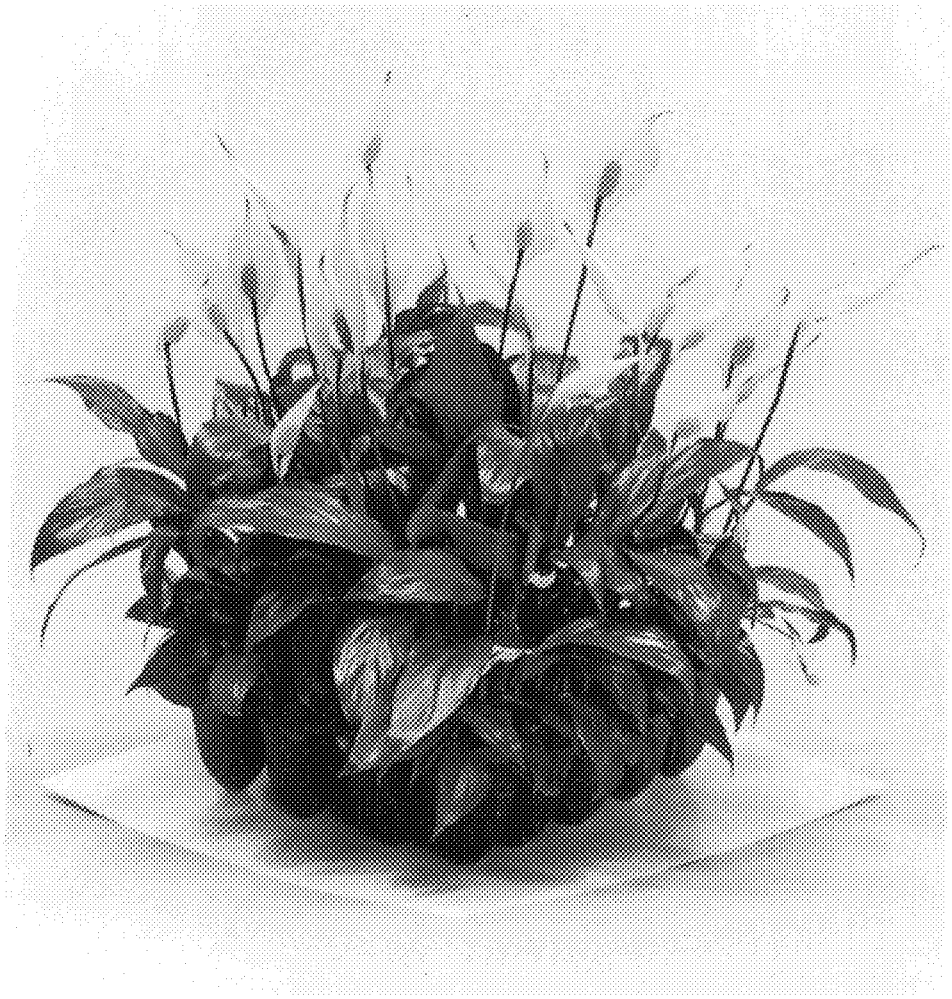

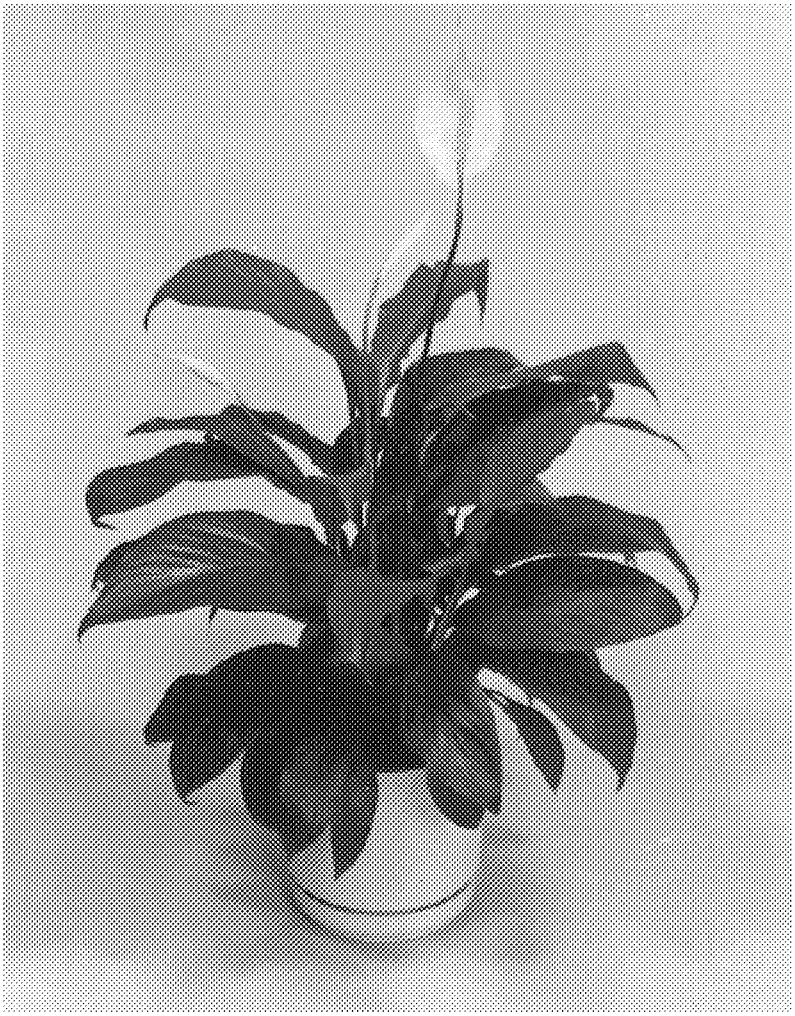

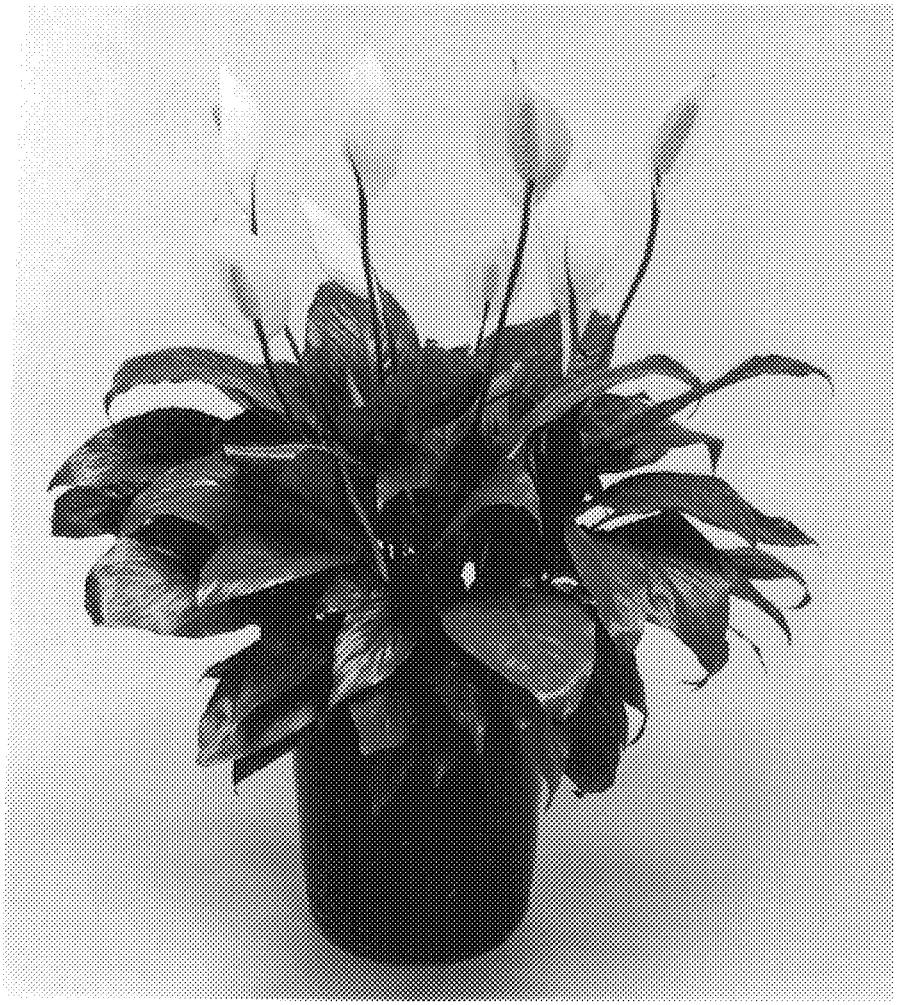

* * * * *